United States Patent [19]
Skrtic

[11] Patent Number: 5,992,211
[45] Date of Patent: Nov. 30, 1999

[54] CALIBRATED MEDICAL SENSING CATHETER SYSTEM

[75] Inventor: Michael M. Skrtic, Johanneshov, Sweden

[73] Assignee: Medtronic, Inc., Minneapolis, Minn.

[21] Appl. No.: 09/064,727

[22] Filed: Apr. 23, 1998

[51] Int. Cl.⁶ ............................ C25C 7/06; G01N 27/61; G01N 27/416; G01N 37/00
[52] U.S. Cl. .................... 73/1.03; 73/864.83; 204/401
[58] Field of Search ............................ 73/1.03, 1.04, 73/864.83; 204/400, 401

[56] References Cited

U.S. PATENT DOCUMENTS

| | | | |
|---|---|---|---|
| 4,340,457 | 7/1982 | Kater | 204/195 R |
| 4,384,927 | 5/1983 | Nichols | 204/32 R |
| 4,618,929 | 10/1986 | Miller et al. | 364/415 |
| 4,635,467 | 1/1987 | Hoffa et al. | 73/1 G |
| 4,689,308 | 8/1987 | Gerhard | 436/18 |
| 4,700,560 | 10/1987 | Hoffa et al. | 73/1 G |
| 4,814,058 | 3/1989 | Bordenick | 204/401 |
| 4,935,106 | 6/1990 | Liston et al. | 204/401 |
| 5,018,527 | 5/1991 | Pfab et al. | 128/635 |
| 5,084,020 | 1/1992 | Gartz | 604/110 |
| 5,145,565 | 9/1992 | Kater et al. | 204/400 |
| 5,188,803 | 2/1993 | Hochberg | 422/102 |
| 5,207,087 | 5/1993 | Costello | 73/1 G |
| 5,246,109 | 9/1993 | Markle et al. | 206/363 |
| 5,278,072 | 1/1994 | Wall et al. | 436/8 |
| 5,293,770 | 3/1994 | Hansen et al. | 73/1 R |
| 5,325,709 | 7/1994 | Lee | 73/61.43 |
| 5,325,853 | 5/1994 | Morris et al. | 128/630 |
| 5,329,804 | 7/1994 | Germany et al. | 73/1 G |
| 5,348,706 | 9/1994 | Abul-Haj et al. | 422/100 |
| 5,420,038 | 5/1995 | Wall et al. | 436/8 |
| 5,505,828 | 4/1996 | Wong et al. | 205/777.5 |
| 5,596,988 | 1/1997 | Markle et al. | 128/635 |
| 5,603,817 | 2/1997 | Settler et al. | 204/433 |
| 5,614,416 | 3/1997 | Lauks et al. | 436/68 |

*Primary Examiner*—Hezron Williams
*Assistant Examiner*—Chad Soliz
*Attorney, Agent, or Firm*—Thomas Woods; Harold Patton; Michael J. Jaro

[57] ABSTRACT

A calibrated medical sensing catheter system in which a catheter-mounted sensor may be calibrated in a simple and reliable manner. In one embodiment the calibration may be performed using a disposable vessel containing two volumes of calibrating fluid, each volume separately accessible by the sensor to be calibrated. Preferably, such a vessel takes the form of an elongated tube having a first volume at one end and a second volume at the other end, each volume containing distinct calibrating fluids. Each volume may be accessed through the respective ends of the tube by introducing a sensor through a pierceable membrane, such as a foil-plastic membrane or seal. In an alternative embodiment the calibrated vessel takes the form of an elongated cylinder having two separate volumes of calibrating fluid separated by a common pierceable membrane or seal. The second embodiment may be used to calibrate a sensor by introducing the sensor into a first volume of the tube and therefore piercing the common pierceable membrane and thus introducing the sensor into the second volume of the vessel. In other embodiments the catheter further features a fitting to facilitate the piercing of the membranes, the fitting designed so as to remain in the vessel once the catheter is withdrawn. In such a manner the vessel may not be reused.

8 Claims, 5 Drawing Sheets

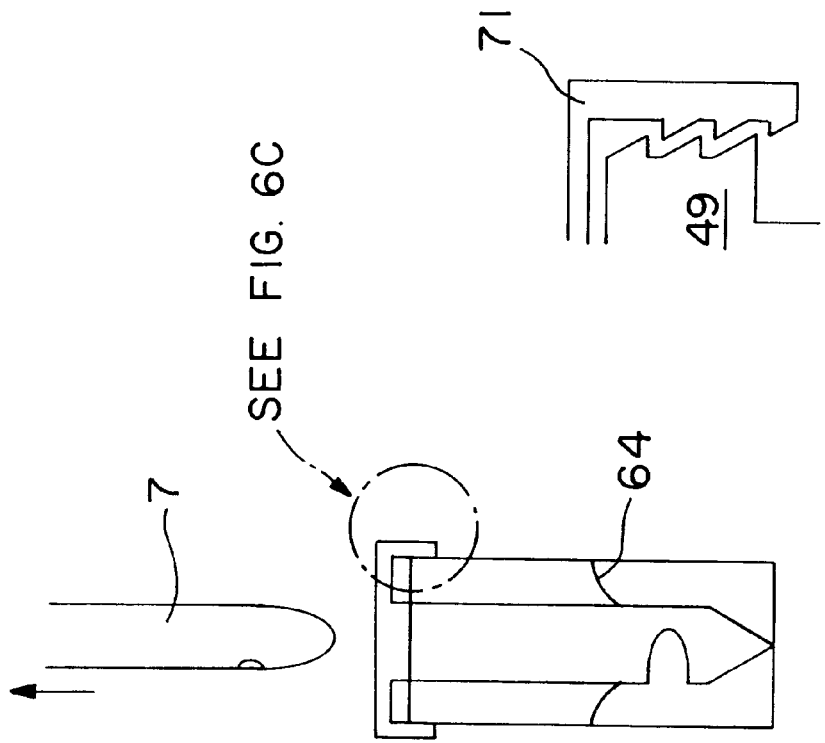
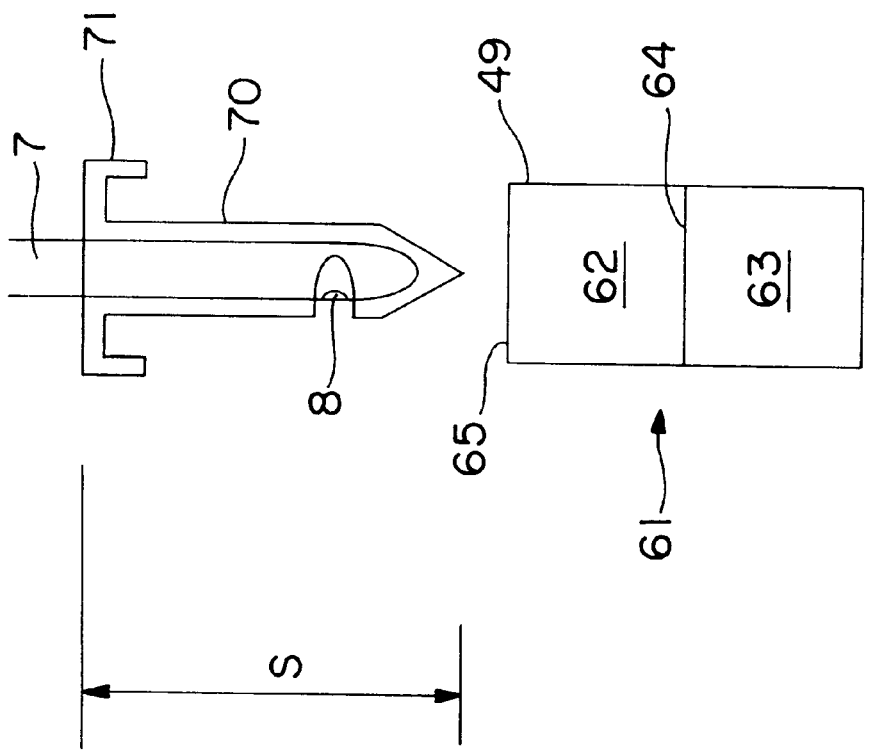
FIG. 6A  FIG. 6B  FIG. 6C

CALIBRATED MEDICAL SENSING CATHETER SYSTEM

FIELD OF THE INVENTION

The present invention relates to the field of calibrated medical sensors and, in particular, to a system in which the sensor may be calibrated in a simple and reliable manner.

BACKGROUND OF THE INVENTION

The use of various sensors to measure gaseous and non-gaseous constituent parameters of fluids has become common in recent years. Such sensors may include electrodes and the like, and are often used to measure constituent parameters of fluids such as biochemical fluids (e.g. blood), natural or sewage water, ferments, laboratory fluids, and the like.

Fluid constituent parameters which are frequently measured by such sensors include partial pressure of a gas constituent (e.g. $pO_2$ and $pCO_2$), pH, concentrations of various ions (e.g. sodium, potassium, calcium, chloride and the like), and concentrations of various organic molecules such as sugars (e.g. glucose), hormones and enzymes.

Prior to an accurate measurement of a fluid constituent parameter, often it is necessary to calibrate a sensor, including its associated instrumentation. Calibration techniques generally involve bringing a sensor into communication with a reference (calibration) liquid having a known concentration of the constituent to be measured.

A calibration fluid may be prepared for immediate use, however, such preparation is time-consuming and requires skill and accuracy. Once a calibration fluid is prepared, care must be taken to prevent interaction of the fluid with the surrounding environment which might alter its make-up and result in faulty calibrations. Such alterations in the make-up of a calibration fluid may result from permeation, diffusion, chemical reaction, and the like.

Because of the time and skill involved in the preparation of a reference fluid, and as a result of the problems associated with maintaining a reference fluid in usable condition over time, sensors are frequently calibrated using pre-packaged calibration fluids.

Two examples of packaging arrangements for reference solutions are described in U.S. Pat. No. 4,340,457 to Kater. One package includes a pair of electrodes for use as a potassium ion sensor, mounted in openings along the length of a cylinder containing a reference fluid. The cylinder has plastic caps at each end to seal the package. After calibration of the sensor, the caps are removed from the cylinder, the fluid is drained, and the cylinder may be inserted into an extracorporeal blood loop for measuring the potassium ion concentration of a patient's blood.

Another package described in the Kater patent includes a stoppered vial containing a reference fluid. A pair of electrodes for use as a potassium ion sensor are mounted in a catheter which is inserted through the stopper bringing the electrodes into communication with the fluid in the vial. After calibration of the sensor, the catheter may be removed from the vial and inserted into a blood vessel for measuring the potassium ion concentration of a patient's blood.

Thus, there remains a need for a system having a calibrated medical sensor which permits calibration to be performed in both a simple and reliable manner.

SUMMARY OF THE INVENTION

The present invention provides a calibrated medical sensing catheter system in which a catheter-mounted sensor may be calibrated in a simple and reliable manner. In one embodiment the calibration may be performed using a disposable vessel containing two volumes of calibrating fluid, each volume separately accessible by the sensor to be calibrated. Preferably, such a vessel takes the form of an elongated tube having a first volume at one end and a second volume at the other end, each volume containing distinct calibrating fluids. Each volume may be accessed through the respective ends of the tube by introducing a sensor through a pierceable membrane, such as a foil-plastic membrane or seal. In an alternative embodiment the calibrated vessel takes the form of an elongated cylinder having two separate volumes of calibrating fluid separated by a common pierceable membrane or seal. The second embodiment may be used to calibrate a sensor by introducing the sensor into a first volume of the tube and therefore piercing the common pierceable membrane and thus introducing the sensor into the second volume of the vessel. In other embodiments the catheter further features a fitting to facilitate the piercing of the membranes, the fitting designed so as to remain in the vessel once the catheter is withdrawn. In such a manner the vessel may not be reused.

BRIEF DESCRIPTION OF THE DRAWINGS

FIGS. 6A–6C are a further alternative embodiment of the present invention.

The FIGS. are not necessarily to scale.

DETAILED DESCRIPTION OF THE DRAWINGS

Figure 1:
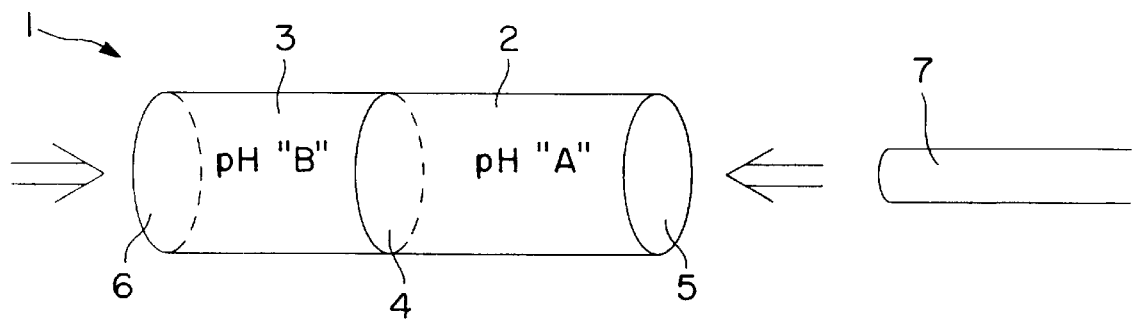
FIG. 1 is a view of a calibration vessel and sensor according to the first embodiment of the invention.

FIG. 1 is a view of a calibration vessel and sensor according to the first embodiment of the invention. As seen, the system, according to the present invention, concerns a calibration vessel 1 and corresponding medical sensing catheter 7. Medical sensing catheter may be any desired, and suitable to the parameter to be sensed in the patient. Catheter may include, for example, any of the several models of Zinetics 24M internal reference catheter, available from Zinetics Medical, Salt Lake City, Utah, U.S.A. As seen, vessel comprises an elongated cylinder having a first volume 2 and a second volume 3 separated by a bulkhead 4. First volume 2 is further preferably sealed by first pierceable membrane 5 while second volume 3 is sealed by second pierceable membrane 6. Pierceable membrane may take any form desired so long as they are both inert to the fluids contained in the volumes 2 and 3 and further pierceable by medical sensor 7. In the preferred embodiment membranes 5 and 6 are a plastic-foil film. Film preferably has a multi-layer structure. The specific structure is chosen depending upon the fluid or fluids contained in each respective volume. The multi-layer film structure may, for example, be a co-extruded film, a coated film or a laminated film. Such a multi-layer film structure may include a seal layer in combination with a barrier film such as polyester, nylon, EVOH, polyvinylidene dichloride (PVDC) such as SARAN™ (Trademark of The Dow Chemical Company), metallized films and thin metal FOCUS foils. The fluids contained within each volume will dictate, in a large degree, the selection of the other material or materials used. Film is further fashioned so as to be readily pierceable, either by catheter itself or by the separate fitting separably fitted with the catheter, as discussed below with reference to FIGS. 5 and 6.

In use, the vessel 1 is used to calibrate the catheter 7 through the individual calibrating fluids contained within first and second volumes 2 and 3 respectively. For example, volume 2 may contain a calibrating fluid containing a pH of 7. Catheter is then pierced through membrane 5 and left for a predetermined period of time in volume 2 and thus in contact with the pH calibrating fluid. Thereafter, catheter 7 is removed from the first volume, the vessel 1 is rotated and catheter is pierced through membrane 6 to bring it into contact with the second calibrating fluid contained in second volume 3.

Figure 2:
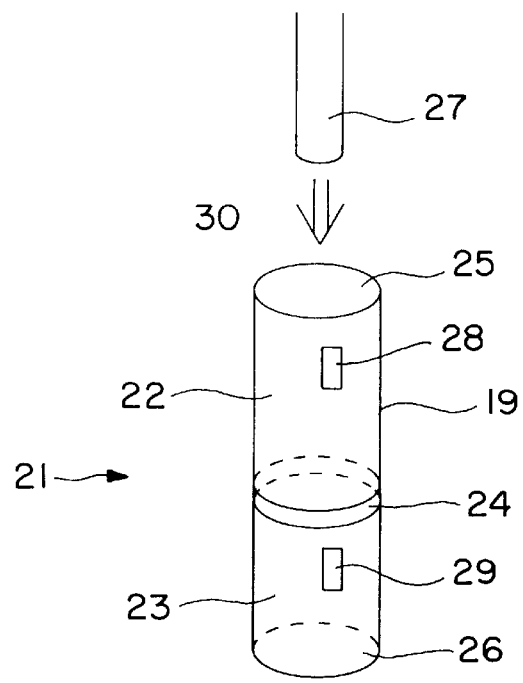
FIG. 2 is a view of a calibration vessel and sensor according to the second embodiment of the invention.

FIG. 2 is a view of a calibration vessel and catheter according to the second embodiment of the invention. As seen, this embodiment is substantially similar to the embodiment shown in FIG. 1 but for the common second pierceable membrane 24 which separates the two calibrating fluids as opposed to the impervious bulkhead in the first embodiment. To be specific, vessel 21 has a first volume 22 and a second volume 23. First volume is defined by cylindrical wall 19, pierceable membrane 25 and second pierceable membrane 24. Second volume is likewise defined using common second pierceable membrane 24, cylindrical wall 19 and impervious bulkhead 26.

In this embodiment the medical catheter 27 is disposed through pierceable membrane 25 and into volume 22 for a predetermined period of time. Pierceable membrane 25 is preferably a foil-plastic film. Volume 22 preferably includes a first calibrating fluid such as one having a pH 7. Thereafter, the medical catheter 27 is further moved in the direction 30 from first volume 22 through second pierceable membrane 24 and thereafter into second volume 23. Membrane 24 is also preferably a foil-plastic film. Second volume 23 preferably contains a second calibrating fluid, such as one having a pH1. Each volume, furthermore, may feature pH indicators 28, 29 disposed within first volume and second volumes respectively to indicate the pH of each respective fluid is in the desired range.

Figure 3:
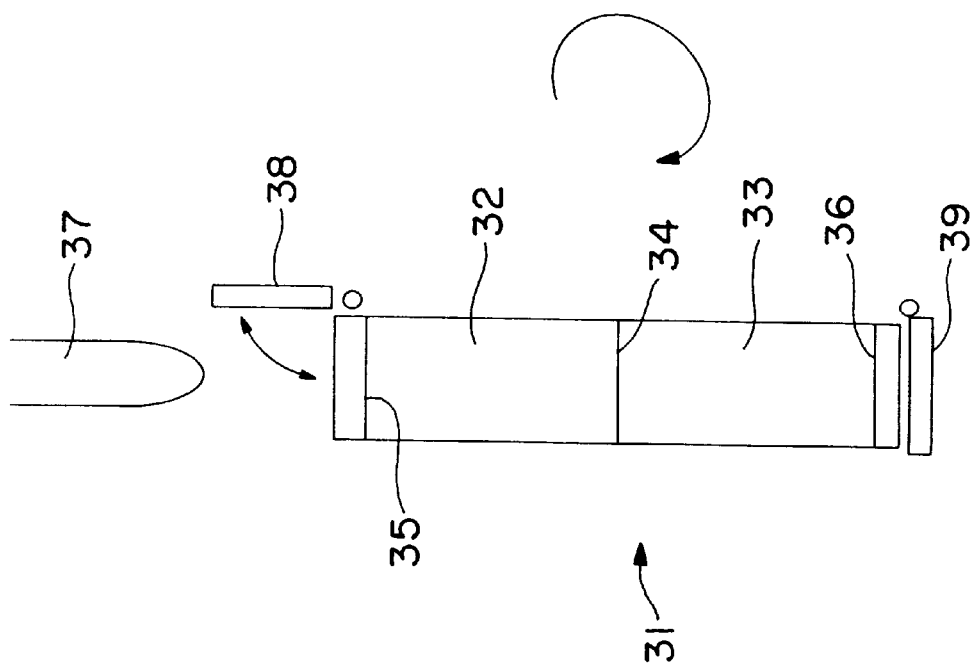
FIG. 3 is a third alternative embodiment of the present invention.

FIG. 3 is a third alternative embodiment of the present invention. As seen, calibration vessel 31 is essentially like that shown in FIG. 1. As seen, the system, according to the present invention, concerns a calibration vessel 31 and corresponding medical catheter 37. Medical catheter may be any desired, and suitable to the parameter to be sensed in the patient. As discussed above, catheter may include, for example, any of the several models of Zinetics 24M internal reference catheter, available from Zinetics Medical, Salt Lake City, Utah, U.S.A. As seen, vessel comprises an elongated cylinder having a first volume 32 and a second volume 33 separated by a bulkhead 34. First volume 32 is further preferably sealed by pierceable membrane 35 while second volume 33 is sealed by pierceable membrane 36. Pierceable membrane may take any form desired so long as they are both inert to the fluids contained in the volumes 32 and 33 and further pierceable by medical catheter 37. In the preferred embodiment membranes 35 and 36 are a plastic-foil film.

This embodiment further features a pair of sealing lids disposed at opposite ends of vessel. In particular, lid 38 is disposed on a first end such that once membrane 35 is broken, the lid may seal volume 32 to thus permit vessel to be rotated without having the contents of volume 32 spill out. After rotation, lid 39 is thereafter raised upwards to permit membrane 36 to be accessible by catheter 37 by piercing membrane 36. Lids and their associated hinges, as well as container itself, are fashioned using a ballistic-type injection molded plastic, although other materials such as glass or metal or any combinations thereof may also be used.

In use, the vessel 1 is used to calibrate the catheter 7 through the individual calibrating fluids contained within volumes 2 and 3 respectively. For example, volume 2 may contain a calibrating fluid containing a pH of 7. Catheter is then pierced through membrane 5 and left for a predetermined period of time in volume 2 and thus in contact with the pH calibrating fluid. Thereafter, the vessel 1 is rotated and catheter 7 is pierced through membrane 6 to bring it into contact with the second calibrating fluid contained in volume 3.

Figure 4:
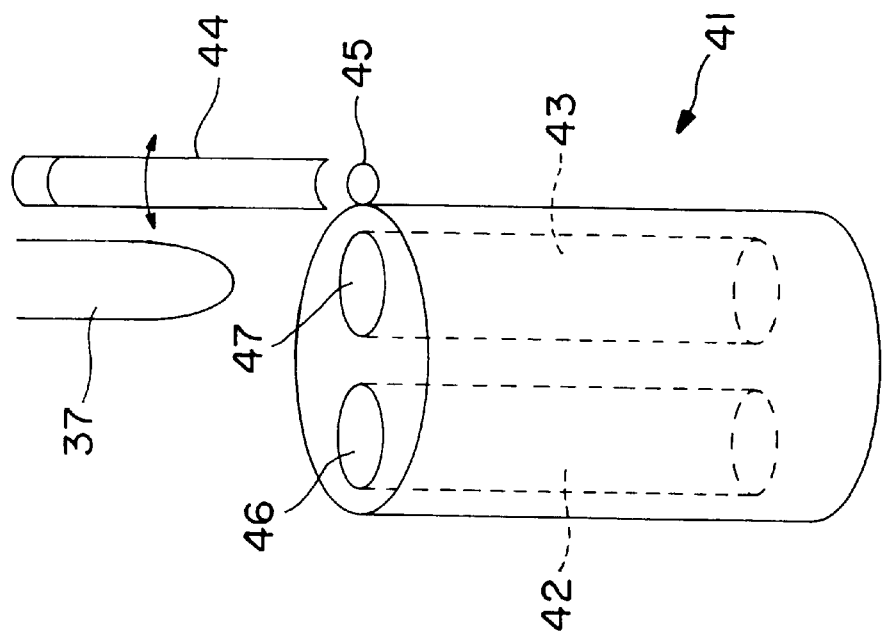
FIG. 4 is a further alternative embodiment of the present invention.

FIG. 4 is a fourth alternative embodiment of the present invention. As seen, calibration vessel 41 is essentially similar to that shown in FIG. 3 but for the fact that first volume 42 and second volume 43 are disposed in a side by side configuration instead of a coaxial orientation. Through this side by side orientation the catheter 37 may be inserted into either of the volumes without requiring the rotation of the vessel or a further piercing of the membrane. Each vessel, moreover, features a pierceable membrane 46, 47, as discussed above. Vessel further includes a lid 44 mounted using a hinge 45 to provide recurring access to each of the vessels.

FIG. 5 depicts a further alternative embodiment of the present invention. In this embodiment the calibration vessel is designed to intimately cooperate with a fitting separably disposed on the catheter. The separable fitting provides the requisite sharpness and structural integrity to permit the catheter to be introduced into each of the respective vessels containing calibration fluid by breaking their respective seals. The fitting is designed to frictionally engage with the outer surface of the catheter and thus remain in place on the catheter end unless forcibly removed. The fitting is further designed so as to cooperate with such a membrane and be removed from the end of the catheter once it has been inserted into the calibration vessel. In such a manner the fitting permits a catheter to be introduced only once into the calibration vessel.

Figure 5C:
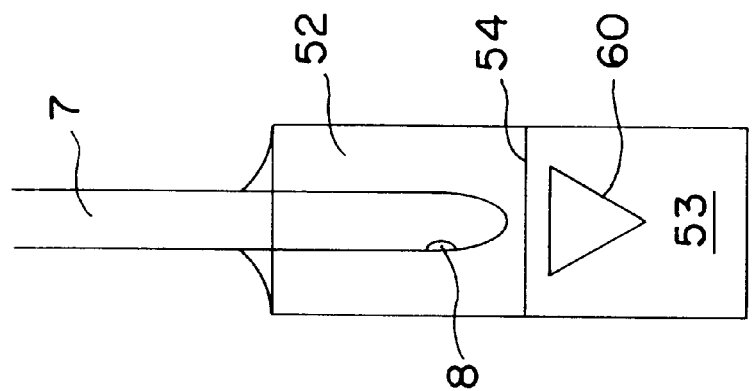
FIGS. 5A–5C are views of a further alternative embodiment of the present invention.
Figure 5B:
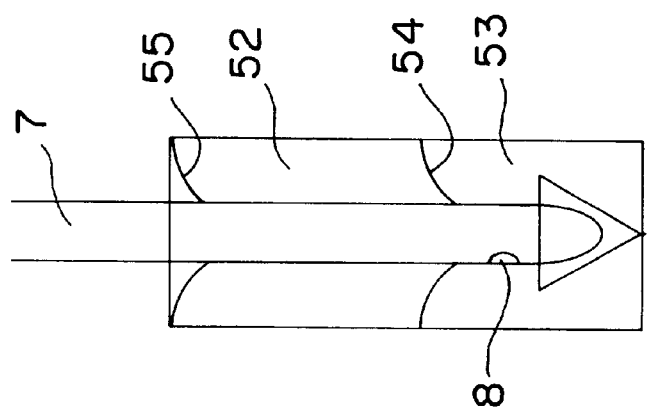
Figure 5A:
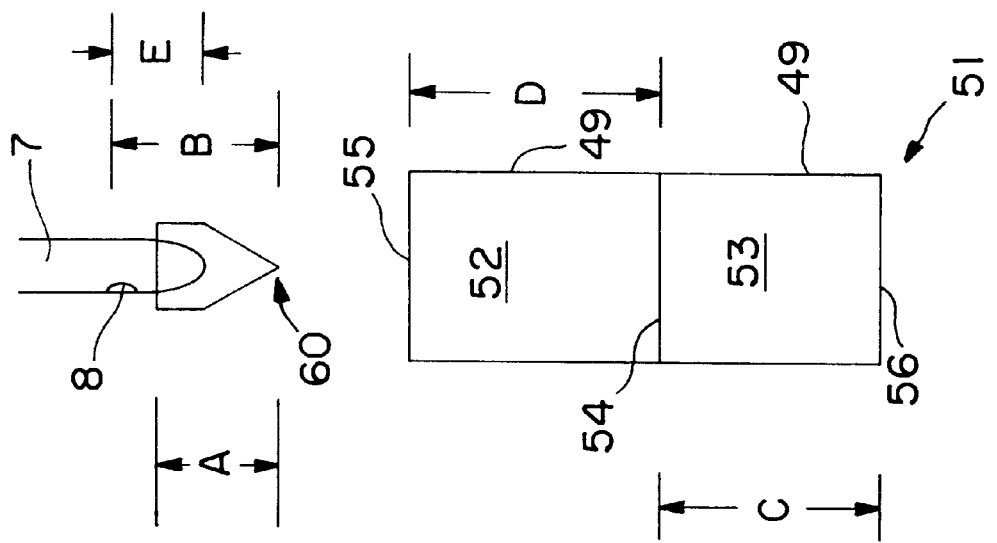

As best seen in FIG. 5A vessel 51 has a first volume 52 and a second volume 53. First volume is defined by wall 49, pierceable membrane 55 and second pierceable membrane 54. Second volume 53 is likewise defined using second pierceable membrane 54, wall 49 and bulkhead 56. Pierceable membranes 54, 55 are constructed using laminate as discussed above. As is further seen, this embodiment requires the use of fitting 60 disposed over the distal end of catheter 7. As seen in this view, it is important that fitting 60 not obstruct fluid access to sensing electrode 8 of the catheter 7.

FIG. 5B best illustrates the operation of calibration vessel and its cooperation with fitting to provide access to respective fluid volumes while further ensuring disposable catheters are used only once with the calibrated system. In FIG. 5B the catheter is shown disposed through membranes 54 and 55 so that electrode sensing portion 8 is contained within and contacts the fluid of volume 53. Once the electrode has sufficiently contacted the fluid of volume 53 the catheter 7 is partially withdrawn such that electrode sensor 8 is thereafter disposed within volume 52, as is best seen in FIG. 5C.

As is further seen in FIG. 5C, the second pierceable membrane 54 cooperates with the fitting 60 so as to remove it off the end of the catheter and maintain it within second volume 53. As can be appreciated, especially with regard to FIG. 5A, the relative dimensions of the respective volumes 52 and 53 as well as the total distance between the tip of the fitting 60 to the ultimate placement of sensing electrode 8 is important. That is, with reference to FIG. 5A dimension B must be less than either dimension C or D.

FIG. 6 is a further alternative embodiment of the present invention. This embodiment is similar to that shown in FIG. 5 but for the fact that an elongated sheath 70 takes the place of fitting 60. Elongated sheath is designed so as to permit electrode sensor 8 to be introduced within second volume 63 once the sheath overhang 71 contacts wall 49. In use elongated sheath is designed so as to permit sensor 8 to be introduced within first volume 62 before permitting sensor to be inserted thereafter into second volume 63. Once sheath is inserted so as to permit sensor 8 to be within second volume 63, overhang 71 mates with and locks into wall 49 as seen in FIGS. 6B and 6C. Thereafter, catheter 7 may be withdrawn from the lumen of sheath 70 and thereafter be inserted into the patient. Due to the locking of sheath 70 with vessel 61 the calibration vessel is thereafter not enabled for use with other medical catheters. Moreover, because the catheter 7 is designed so as to not have the requisite pierceability or rigidity to permit its own through pierceable membrane 64, 65, such a medical catheter may thereafter not be reused with a similar type calibration vessel.

Figure 7A:
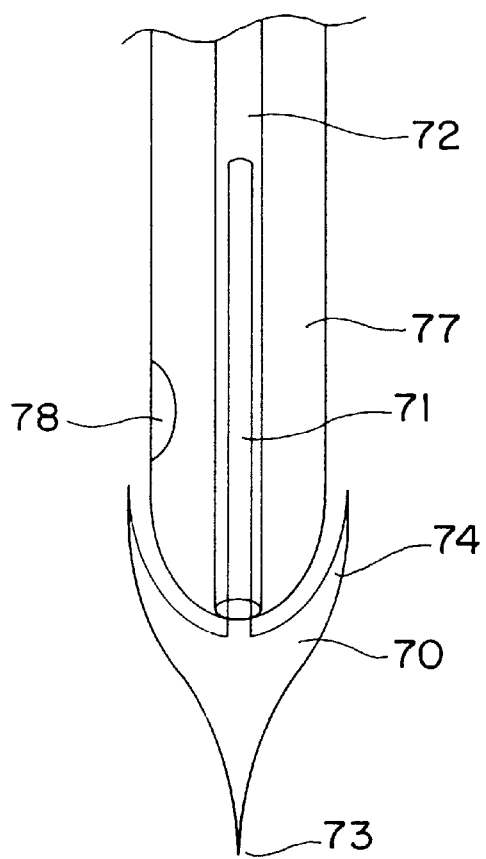
FIGS. 7A and B depicts a further alternative embodiment of the present invention.
Figure 7B:
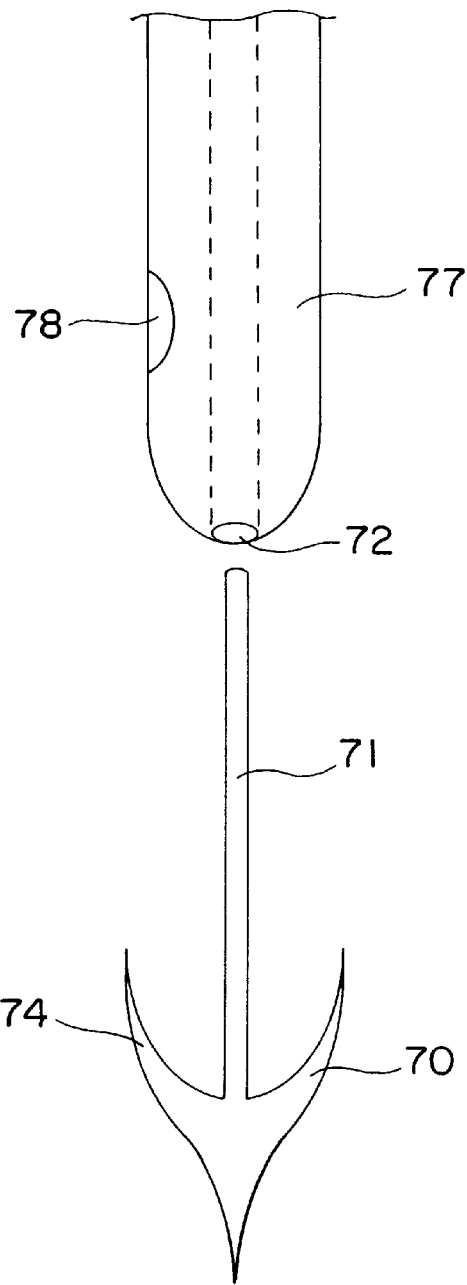

FIGS. 7A and B depicts a further alternative embodiment of the present invention. In this embodiment the fitting separably disposed on the catheter is provided so as to have a center elongated portion fit within a lumen of the catheter. The center elongated portion provides enhanced rigidity to the catheter so as to better facilitate piercing the pierceable membranes of the calibration vessel. Like the fitting described above in FIG. 5, this fitting is also designed so as to engage with one of the pierceable membranes and thus be removed from the end of the catheter as the catheter is withdrawn from the calibration vessel. In such a manner this embodiment of fitting permits a catheter to be introduced only once into the calibration vessel while further enhancing the rigidity of the catheter so as to be pierced into membrane. FIG. 7A shows a fitting 70 disposed on the end of catheter 77. Catheter is like those already described above and has a pH sensor 78 but for the fact that in this embodiment catheter has a center lumen 72. As seen fitting 70 has an elongated center portion 71 which fits within the center lumen 72 provided within the end of catheter. As further seen fitting has an arrow-head shaped end 73 to facilitate piercing one or more of the membranes. Like the fitting described above, the shoulders 74 of the fitting are disposed so as to engage with membranes and thus facilitate the removal of fitting from the end of catheter while the catheter is removed from the calibration vessel. FIG. 7B shows a fitting 70 removed from an end of catheter 70.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A calibrated medical sensing catheter system comprising:

a container for containing a first calibration fluid in a first volume and a second calibration fluid in a second volume, container having a first pierceable membrane to provide access to the first volume, a second pierceable membrane to provide access to the second volume, a medical sensing catheter, the medical sensing catheter adapted to be disposed within the first volume and the second volume, and means for piercing capable of piercing the first and second membranes wherein the medical sensing catheter has a lumen, and wherein the means for piercing the first and second membranes comprises a rigid fitting having an elongated portion disposed to fit within the lumen, the elongated portion thereby enhancing the rigidity of the catheter in the region into which the elongated portion is disposed wherein the fitting having means for engaging with the first membrane as the sensing catheter is removed from the first volume to thereby dislodge the fitting from the sensing catheter and cause the fitting to remain in the first volume as the sensing catheter is withdrawn from the first volume.

2. The system of claim I wherein the second pierceable membrane is disposed between the first volume and the second volume.

3. The system of claim 1 wherein the means for piercing is a separate means for piercing component from the medical sensing catheter.

4. The system of claim 1 wherein the means for piercing comprises a rigid fitting which removably fits onto a distal end of the sensing catheter, the fitting having means for engaging with the second membrane as the sensing catheter is removed from the second volume to thereby dislodge the fitting from the sensing catheter and cause the fitting to remain in the second volume as the sensing catheter is withdraw from the second volume.

5. The system of claim 3 wherein the fitting has means for frictionally engaging with the outer surface of the catheter and thus remain in place on the catheter end unless forcibly removed.

6. The system of claim 1 wherein the first pierceable membrane comprises a plastic-foil film.

7. A calibrated medical sensing catheter system comprising:

means for containing a first calibration fluid in a first volume and a second calibration fluid in a second volume, the means for containing having a first pierceable membrane to provide access to the first volume a sensing catheter, means for piercing capable of piercing the first pierceable membrane separably disposed at the distal end of the sensing catheter, the means for piercing capable of piercing the first membrane as the sensing catheter is moved in a first pierceable direction through the first membrane, the means for piercing having means for engaging with the first pierceable membrane and removing the means for piercing from the sensing catheter as the sensing catheter is moved in a second opposite direction through the first membrane.

8. The system of claim 4 wherein the means for containing a first calibration fluid in a first volume and a second calibration fluid in a second volume further comprises a second pierceable membrane to provide access to the second volume.

* * * * *